United States Patent [19]

Haider

[11] Patent Number: 5,107,556

[45] Date of Patent: Apr. 28, 1992

[54] FURNITURE SUSPENDED FROM ROPES

[76] Inventor: Eduard Haider, Dechantseeser Str. 4, D-8591 Pullenreuth, Fed. Rep. of Germany

[21] Appl. No.: 477,990

[22] PCT Filed: Aug. 25, 1989

[86] PCT No.: PCT/DE89/00565
§ 371 Date: Apr. 23, 1990
§ 102(e) Date: Apr. 23, 1990

[87] PCT Pub. No.: WO90/01886
PCT Pub. Date: Mar. 8, 1990

[30] Foreign Application Priority Data

Aug. 28, 1988 [DE] Fed. Rep. of Germany ... 8810986[U]

[51] Int. Cl.[5] ............................................. A63G 9/00
[52] U.S. Cl. .......................................... 5/124; 5/103; 248/370; 297/273
[58] Field of Search ................. 5/101, 103, 107, 118, 5/124, 241, 244; 248/370, 610; 297/273, 281, 282

[56] References Cited

U.S. PATENT DOCUMENTS

| 923,974 | 6/1909 | Johnson | 248/370 |
|---|---|---|---|
| 1,689,397 | 10/1928 | Lee | 297/281 |
| 2,567,611 | 9/1951 | McGehee | 5/124 |
| 2,567,612 | 9/1951 | McGehee | 5/124 |
| 4,567,614 | 2/1986 | Haider | 5/103 |
| 4,615,059 | 10/1986 | Darowski | 297/273 |
| 4,783,863 | 11/1988 | Degen | 5/244 |
| 4,793,009 | 12/1988 | Degan | 5/103 |
| 4,868,939 | 9/1989 | Tagtow | 5/103 |

FOREIGN PATENT DOCUMENTS 3506377 8/1986 Fed. Rep. of Germany ...... 297/273

Primary Examiner—Renee S. Luebke
Assistant Examiner—F. Saether
Attorney, Agent, or Firm—Jordan and Hamburg

[57] ABSTRACT

Sitting or reclining furniture with an upper and a lower part that can move relative to each other. The upper part is suspended so as to be able to oscillate on the lower part and at least two sets of ropes are arranged functionally in series. One set of ropes is suspended by way of bridge pieces and an approximately gallows-like frame. The bridge pieces are, in turn, joined to each other through the frame.

15 Claims, 4 Drawing Sheets

FURNITURE SUSPENDED FROM ROPES

BACKGROUND OF THE INVENTION

The present invention relates to furniture for sitting or reclining.

There have already been a number of attempts made to replace sitting and reclining furniture, which up to now has been static, with dynamic furniture.

Rocking chairs have been known for a very long time; these incorporate a dynamic component, unlike other conventional chairs. The same applies to cradles, which have also been known for a very long time; these are particularly well-liked by children on account of their dynamic character and, in addition, promote sleep because of this characteristic.

Recently, the water bed has appeared on the market as a modern version of a dynamic bed. However, the water bed entails considerable disadvantages in that it takes up a relatively large amount of space, reacts very slowly to movement, is very heavy, and extremely costly. In addition, if the water leaks out, it can cause considerable damage. In addition, the water bed does not provide any continuous up and down movement and cannot provide a constantly even horizontal surface.

CH-PS No. 242 273 describes a seat that is supported on a hinged support and which is in steady equilibrium, from which position it can be deflected to a greater or lesser degree when loaded.

DE-GM 1 708 191 describes a seat that is installed on a rocking frame that can be locked if required. Such a rocking frame is not suitable for use in a bedroom or living room, however.

GB-PS No. 696 239 describes a rocking chair that can be move back and forth to a certain extent by a hinge system. Because of the friction that is generated at the hinge points, however, it requires a not inconsiderable amount of force to move it. Any sort of post-oscillation is precluded for all practical purposes.

DE-GM No. 8 222 691 describes a suspension that uses ropes, in which only a negligible amount of damping of the oscillatory movement takes place. In this known solution, however, there is only one characteristic frequency of the oscillating system, this resulting from the oscillating mass and the length of the ropes.

DE-PS No. 3 506 377, which constitutes a special category, describes oscillating, suspended sitting or reclining furniture; this incorporates a plurality of ropes that are connected functionally in series and are of different lengths and which therefore have different, adjacent characteristic frequencies.

It is the task of the present invention to create dynamic sitting or reclining furniture that even in the case of small impulses provides for almost undamped movement of not inconsiderable amplitude.

The solution entails the considerable advantage that even small impulses lead to relatively large oscillatory movements. The desired effect is enhanced thereby.

The present invention is described in greater detail below on the basis of an embodiment shown in the drawings appended hereto.

BRIEF DESCRIPITON OF THE DRAWINGS

DESCRIPTION OF THE PREFERRED EMBODIMENTS

Figure 1:
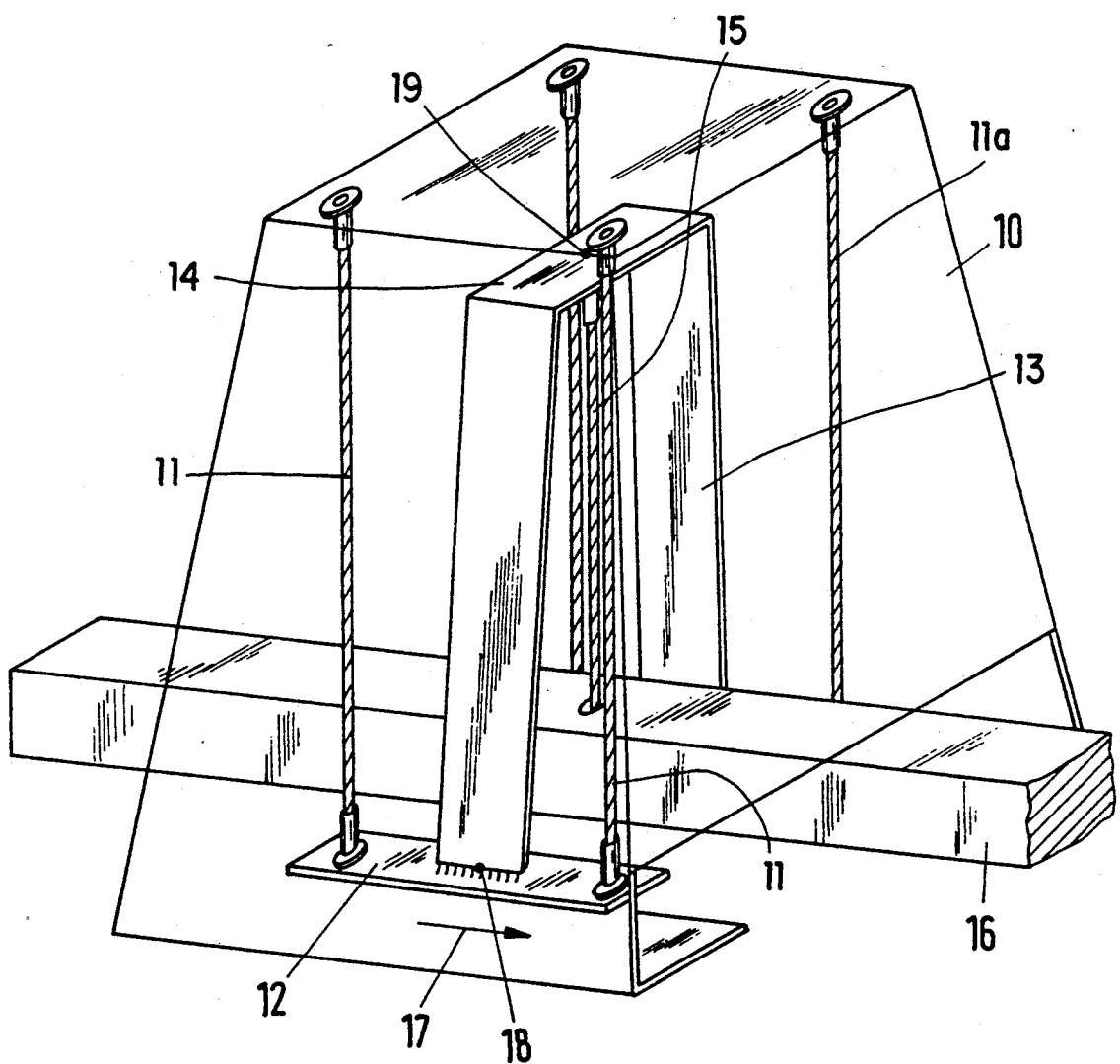
FIG. 1 is a diagrammatic representation of a rope suspension.
Figure 5:
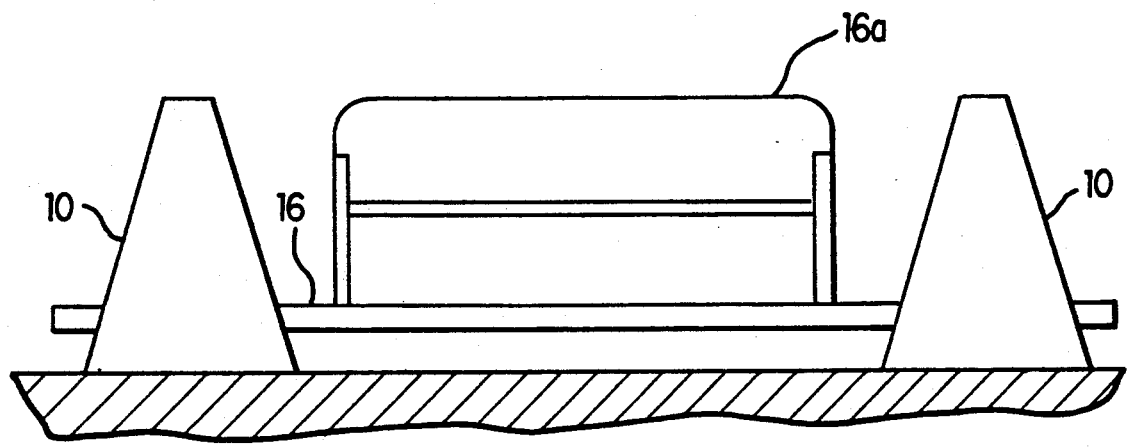
FIG. 5 is a diagrammatic view on a smaller scale showing the furniture.
Figure 6:
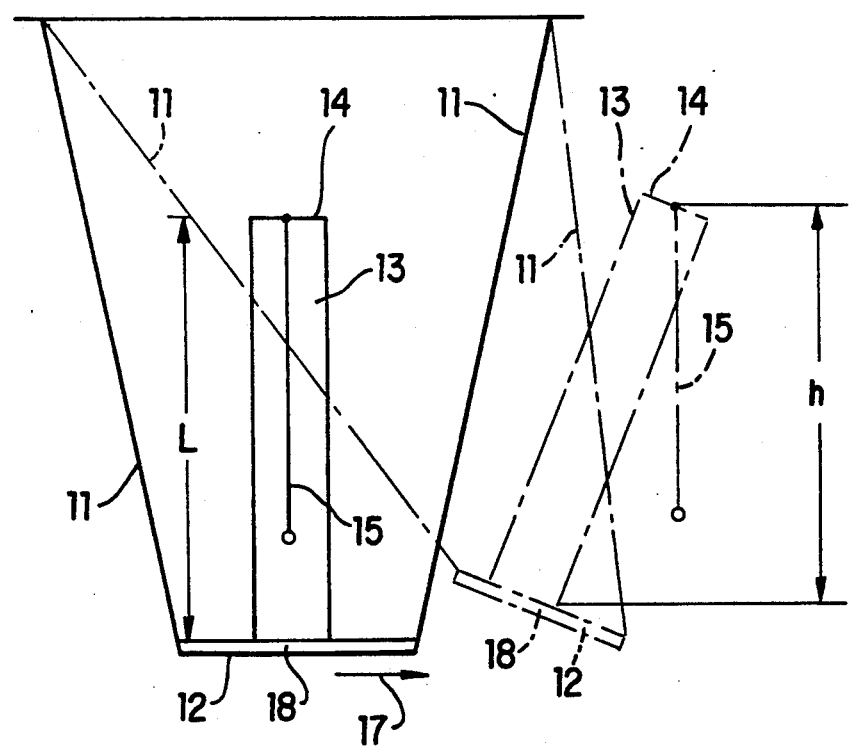
FIG. 6 is a diagrammatic representation of an alternate embodiment.

In FIG. 1, a total of four ropes 11, 11a are arranged in a housing 10 that in the embodiment shown is shaped like a truncated pyramid and stands on a solid base, for example, a floor, arranged in pairs, these ropes support a freely suspended bridge piece 12 and together with this bridge piece they form a trapezoid in such a manner that a right angle is formed as shown in FIG. 1 or an acute or an obtuse trapezoidal angle is formed as shown in FIG. 6. FIG. 1 shows the unswung position of the ropes. In FIG. 6, the unswung position is shown in solid lines and a swung position is shown in broken lines. In a mirror image to the arrangement of ropes 11 and bridge piece 12 there are additional ropes 11a with an associated bridge piece arranged within the housing 10, and in combination these form a second trapezium with the same trapezoidal angle. The two trapeziums 11, 12 or 11a respectively are connected rigidly with each other through an essentially gallows-like frame 13 that can also be in the shape of a trapezium. On the upper cross-beam 14 of the gallows-like frame 13 there is at least one additional rope 15 that supports a support 16 of the movable upper part of the sitting or reclining furniture 16a (FIG. 5) at its lower end. When the two trapeziums 11, 12 or 11a, respectively, make an oscillating movement in the direction indicated by the arrow 17, as shown in FIG. 6 the bridge piece 12 simultaneously makes a slight clockwise tilting movement thereby raising the foot 18 of the frame 13. Since the frame 13, which is also connected to the bridge-piece 12 simultaneously makes a small clockwise tilting movement, the height differential between the foot 18 and the suspension point 19 for the rope 15 on the frame 13 is reduced as can be seen by comparing "L" and "h" in FIG. 6. Thus, the height of the support 16 that is suspended on the rope 15 changes very slightly. This results in greater oscillation amplitudes, which is most desirable in the present case.

Pendulum systems with various characteristic frequencies can be produced by various lengths of the ropes 11 or 11a, on the one hand, and 15 on the other.

Figure 2:
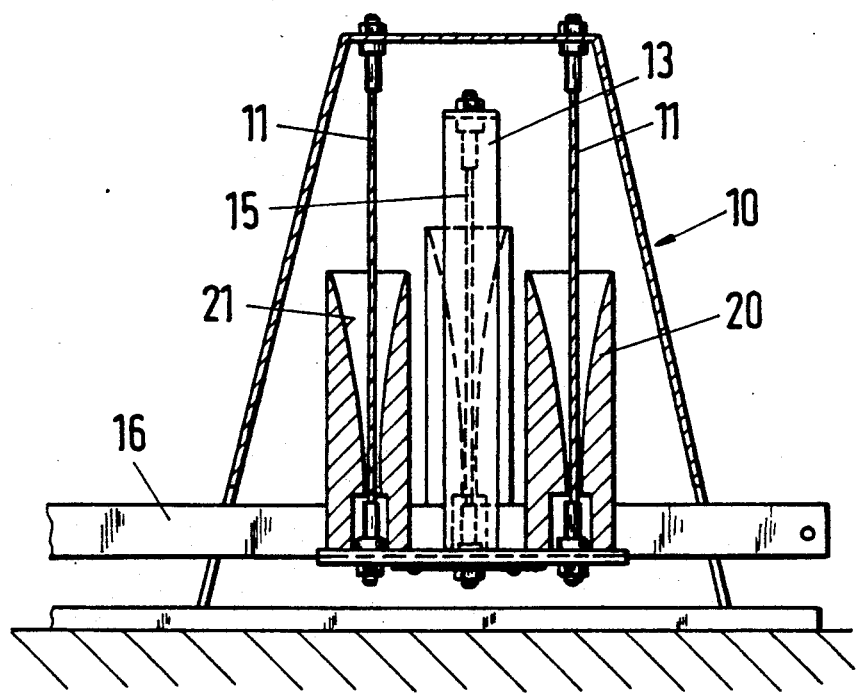
FIG. 2 is a rope system as in FIG. 1 with bevelled fittings that enclose the ropes.

FIG. 2 shows a frame 10 with the ropes 11, a gallows-like frame 13 and a rope 15 in cross-section in the direction of the support 16. In FIG. 2, the individual ropes 11 or 15, respectively, are surrounded by bevelled fittings 21, the inside, unobstructed cross-sections of which taper towards the bottom. The unobstructed cross-sections can be of either circular or oval cross-section. With a circular cross-section, the behavior is the same in all directions, but with an oval cross-section the behaviour in the direction of the longitudinal axis is different to the behaviour in the direction of the transverse axis. Depending on whether the same or different behavior is desired in all directions, one or the other unobstructed cross-section of the bevelled fitting 21 can be selected. At amplitudes that exceed a certain magnitude, the ropes 11 or 15 are adjacent to the unobstructed cross-section of the bevelled fitting 21 up to a specific level and thus reduce the effective length of the rope and thus the characteristic frequency of the rope 11 or 15, respectively, such that a further increase of the amplitude is avoided, this being done gently and without any jarring.

Figure 3:
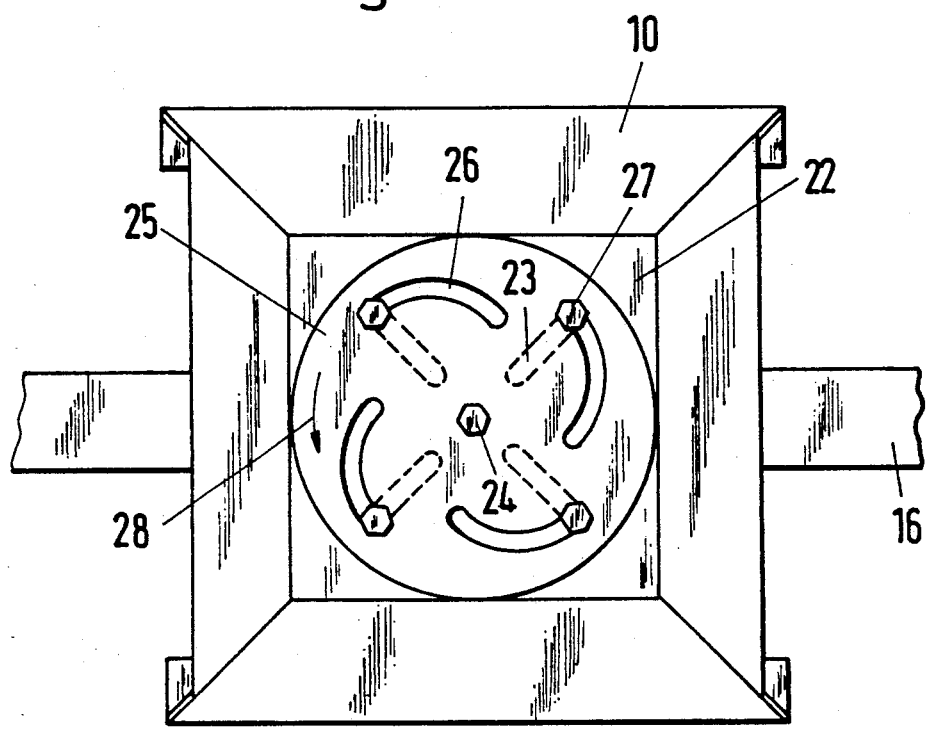
FIG. 3 is a plan view of a rope system with an adjusting disk.
Figure 4:
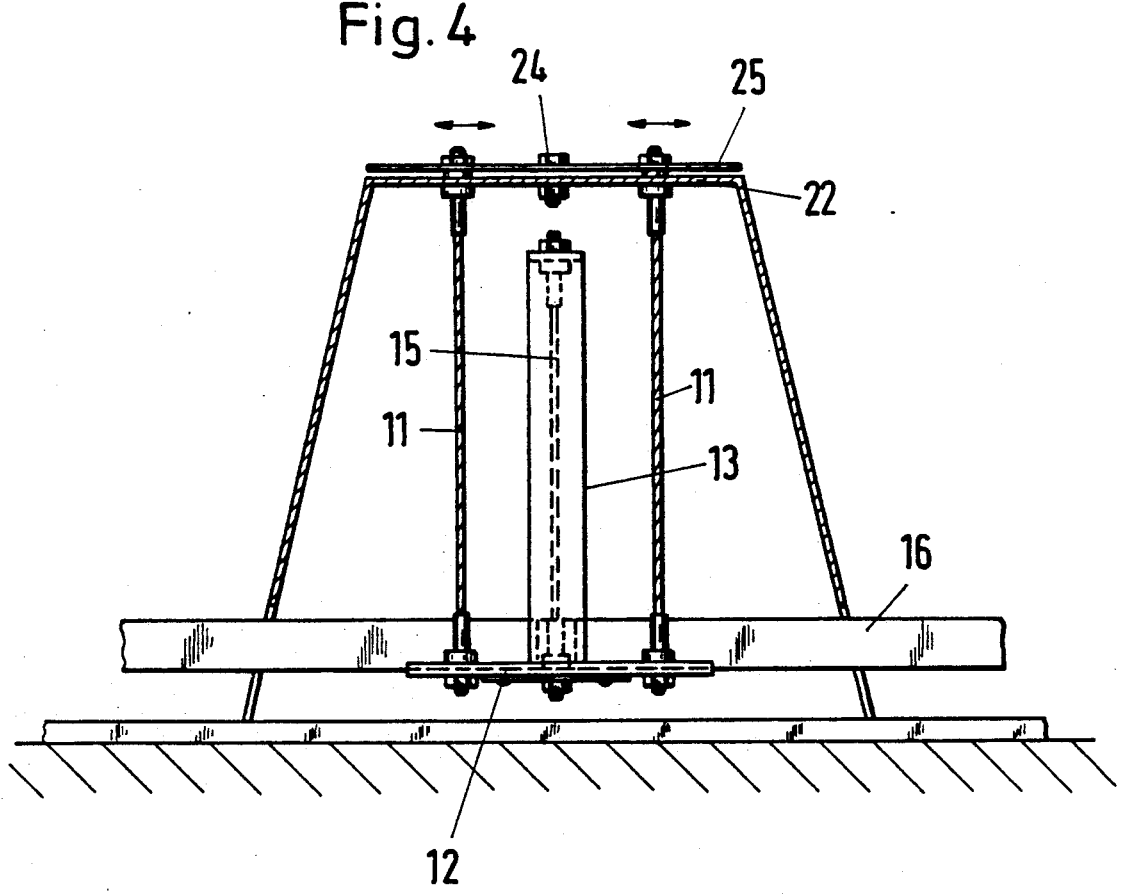
FIG. 4 is a side view of a rope system with an adjusting disk.

In the pendulum system that is shown in plan view in FIG. 3, the upper cover plate 22 of the frame 10 incorporates slots 23 that extend radially in the direction of a common center point 24. On the cover plate 22 there is a disk 25 that rotates about the center point 24 and incorporates essentially spiral slots 26. The ropes 11 are so suspended by suspension points 27, which can also be shaped as nuts, that they pass through both the radial slots 23 of the cover plate 22 of the frame 10 and through the essentially spiral slots 26 in the disk 25 that can rotate about the center point 24. When the disk 25 is moved in the direction indicated by the arrow 28, the upper suspension points for the ropes 11 move in the direction of the center point 24. This can result, for example, in a rectangular trapezium being formed from a trapezium by the ropes and the bridge piece, that is open at the top, and on further rotation a trapezium that tapers towards the top is formed. Thus, there is the potential for continuous adjustment of the trapezium that is formed by the ropes and the bridge piece, and for a continuous influence on the oscillatory behaviour thereby. Thus the user can adapt the oscillatory behaviour according to his wishes and requirements through an infinite range. When the ropes 11 are adjusted so as to be parallel, this will result in normal oscillatory behaviour. The oscillatory behaviour will deviate from the normal case, depending on the degree of variation from the parallel position of the ropes 11 in one or the other direction.

The embodiments of the invention in which an exclusive property or privilege is claimed are defined as follows:

1. Furniture comprising a support structure, two pairs of spaced ropes suspended from said support structure, a pair of generally parallel bridges, each of said bridges being connected to one of said pairs of spaced ropes, an inverted U-shaped member having two spaced parallel legs and a cross-piece, each of said legs having a lower end rigidly affixed to one of said bridges, said cross-piece extending generally perpendicular to said pair of parallel bridges, rope means suspended from said cross-piece and extending between said spaced parallel legs, and a furniture structure suspended from said rope means, said rope means comprises at least one rope which is shorter than each of the ropes of said two pairs of spaced ropes.

2. Furniture according to claim 1, wherein each of said bridges comprises an elongate member having a longitudinal axis, said cross-piece comprising an elongate member having a longitudinal axis which is perpendicular to the longitudinal axis of the elongate member of said bridges.

3. Furniture according to claim 1, wherein one of said pairs of spaced ropes are disposed in a first plane and the other of said pair of spaced ropes are disposed in a second plane, said first and second planes being parallel to one another, said cross-piece comprising an elongate member having a longitudinal axis which is perpendicular to said first and second parallel planes.

4. Furniture according to claim 1, wherein each rope of said two pairs of spaced ropes are of equal length.

5. Furniture according to claim 1, wherein each of said pairs of spaced ropes have an unswung position, each of said ropes of said pairs of ropes being generally vertically disposed when in said unswung position.

6. Furniture according to claim 1, wherein each of said pair of spaced ropes have an unswung position, each of said ropes of said two pairs of ropes being disposed at an acute angle relative to vertical when in said unswung position.

7. Furniture according to claim 6, wherein each rope of a pair of ropes converge towards one another as the respective bridge is approached when each of said pair of spaced ropes are in said unswung position.

8. Furniture according to claim 1 further comprising beveled fittings mounted on each of said bridges, each of said beveled fittings having an elongated passage having a longitudinal axis, each of said ropes of said two pairs of spaced ropes passing through a central passage of one of said beveled fittings, each of said elongated passages having a cross-sectional area which progressively changes along the longitudinal axis of the respective passage.

9. Furniture according to claim 8, wherein said cross-sectional area has a circular configuration.

10. Furniture according to claim 8, wherein each of said cross-sectional areas has an oval cross-sectional configuration.

11. Furniture according to claim 8, wherein each of said passages has an inner passage wall, said inner passage wall having an arcuate configuration when viewed along a diametrical cutting plane which contains said longitudinal axis.

12. Furniture according to claim 1, wherein said support structure have an upper support plate, said support plate having linear slots, a disk overlying said upper support plate, rotatable support means rotatably supporting said disk on said support structure, said disk having an arcuate slot associated with each linear slot such that each arcuate slot partly overlies a part of an underlying associated linear slot, each rope of said two pairs of ropes extending through associated arcuate and linear slots with each rope of said two pairs of ropes being supported by said disk such that rotation of said disk effects movement of each rope of said two pairs of ropes along said linear slots.

13. Furniture according to claim 12, wherein said disk is rotatable about a central axis, said linear slots being disposed along radii extending from said central axis.

14. Furniture according to claim 12, wherein said arcuate slots have a spiral configuration.

15. Furniture according to claim 12, wherein each rope of said two pairs of ropes has an upper end having an enlarged suspension head which overlies said disk to suspend each rope of said two pairs of ropes from said disk.

* * * * *